March 12, 1974 A. W. ELLIS ET AL Plant Pat. 3,518
ROSE PLANT
Filed Oct. 13, 1972
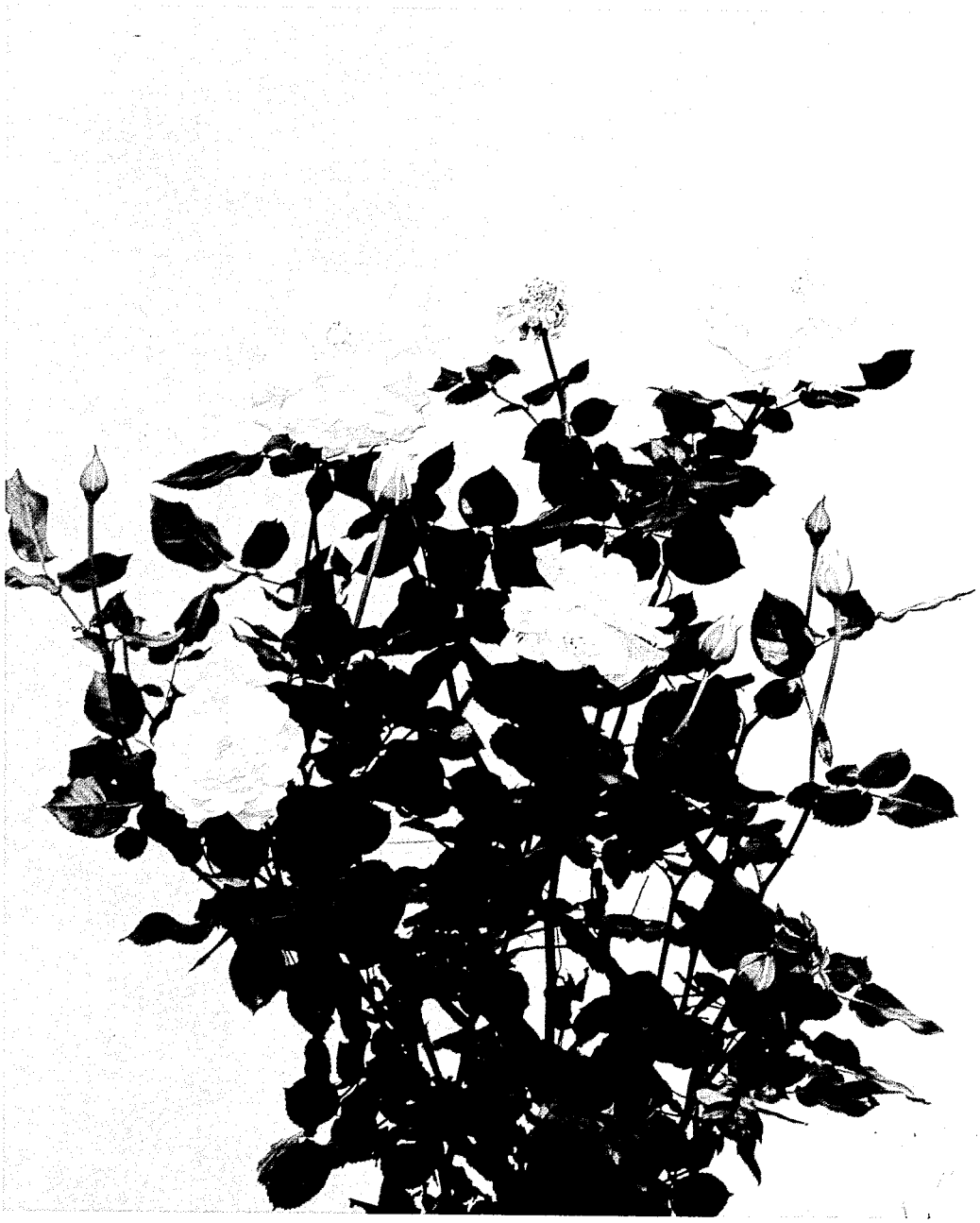

United States Patent Office

Plant Pat. 3,518
Patented Mar. 12, 1974

3,518
ROSE PLANT

Arnold W. Ellis, Upland, and Herbert C. Swim, Ontario, Calif., assignors to Armstrong Nurseries, Inc., Ontario, Calif.

Filed Oct. 13, 1972, Ser. No. 299,912
Int. Cl. A01h 5/00
U.S. Cl. Plt.—24 1 Claim

ABSTRACT OF THE DISCLOSURE

A new variety of rose plant of the Floribunda class, having a tendency to flower heavily and to bear many of its blooms singly, on relatively straight stems which are valuable for cutting because of their length and caliper. Blooms have a strong spicy fragrance, are brilliant yellow in color as they open, and fade only slightly after opening. Stems have very few thorns and prickles, and peduncles are almost free of stipitate glands. The plant has better than average resistance to mildew. Its blooms are large for the class, and they range from 2½ to 3¼ inches in diameter with from 30 to 50 petals plus 2 to 6 petaloids. The petals are undulated in form throughout the life of the bloom.

This invention relates to a new variety of rose of the floribunda class. It is a seedling of the bush type, grown in the greenhouse, for cut flowers. It was discvovered and invented by Arnold W. Ellis and Herbert C. Swim, of Upland and Ontario, Calif., respectively. Its seed parent is Gold Strike (Plant Pat. No. 1,435) and its pollen parent Golden Garnette (Plant Pat. No. 1,898). The new cultivar holds its distinguishing characteristics through succeeding propagations by budding.

The plant presently described was grown in a five-gallon container in a greenhouse at Ontario, Calif. It usually bears its blooms singly, although sometimes two or three to a stem, on strong medium to long stems. The bloom is abundant in the greenhouse, and is nearly continuous throughout the growing season. The fragrance is strong and spicy.

The new cultivar differs from its seed parent, Gold Strike, in several ways, including the following:

It bears its blooms singly more often, and in clusters significantly less often, than does Gold Strike. The petals of the new cultivar are wider in relation to their length, that is, they are more broadly obovate than petals of Gold Strike.

The new cultivar has very few large or small prickles on its stems and branches, whereas on Gold Strike there are several long and sharp prickles on its main stems and branches.

The new cultivar has no stipitate glands and few hairs on its peduncles, whereas Gold Strike has many stipitate glands and many hairs on its peduncles.

The flowers of the new cultivar are, on the average, somewhat larger than the Gold Strike parent, the latter being normally 2 to 2½ inches in diameter, whereas the new cultivar will range from 2½ to 3¼ inches in diameter when grown under favorable conditions as described.

The new cultivar characteristically has about 80 pistils on the average, whereas Gold Strike usually has only about 60 pistils per flower.

The new cultivar differs from its pollen parent, Golden Garnette, in several ways, including:

The plant has stems which are notably straighter and longer than the stems of Golden Garnette, and carries fewer large prickles on its stems and branches than Golden Garnette. Furthermore, the peduncles of the new rose characteristically have fewer hairs than those of Golden Garnette, which may have many hairs.

The flowers of the new cultivar are more fragrant than the flowers of Golden Garnette and, although they fade somewhat at the margins, significantly less fading occurs on the petals of the new cultivar than on the petals of Golden Garnette. The number of pistils in flowers of the new cultivar averages about 80, whereas Golden Garnette will have about 50 pistils per flower, when grown under comparable conditions.

The accompanying drawing illustrates the plant in color, and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length and average caliper. It is erect and almost smooth, with some hairs. Its color is near Strong Yellow Green, 5GY6/8.

Before the calyx breaks, it is small to medium size, for its class, short to medium-length, pointed and ovoid. As the calyx breaks, it has a color ranging from near Brilliant Yellow, 2.5Y9/9, to near Vivid Yellow, 2.5Y8/12.

The inner surface of the sepals carries a fine tomentum, the margins of alternate sepals being lined with a fine wooly tomentum, while the margins of others have some stipitate glands and a few small, narrow foliaceous appendages; sepal apices sometimes have small foliaceous parts; outer surface of sepals is relatively smooth.

As the first petal opens, it is average in size for this class, short to medium-length, and urn-shaped. Its color on the outside is near Vivid Yellow, 5Y8/12, becoming lighter near its apical margin to a color near Brilliant Yellow, 5Y9/9. The inside coloration is the same as the outside surface.

The bud opens up well, and is not retarded, or prevented from opening, by cold, hot, or dry weather.

BLOOM

When fully open, the bloom is large in size, being from 2½ to 3¼ inches in diameter. Its petalage is double, with from 30 to 50 petals, plus 2 to 6 petaloids arranged regularly. In form, it is cupped to high centered at first, becoming open to cupped to high centered. At first, the petals remain cupped, with tips reflexed outward; later, at maturity, they are somewhat more loosely cupped, with tips reflexed outward. Petals are undulated throughout the life of the bloom.

PETALS

The petals are of medium thickness, with both inner and outer surfaces slightly shiny to satiny. The outside petals are nearly round to broadly obovate. The intermediate petals are broadly obovate to obovate. The inside petals are broadly obovate to irregular. All petals are undulated throughout the life of the bloom. The color may be modified by fading slightly and gradually.

The description which follows is of a rose that was newly opened in the month of June, from a rose plant grown in a five-gallon can in a greenhouse, in Ontario, Calif.:

The outer surface of the outside petal was between Brilliant Yellow, 2.5Y9/9, and Brilliant Yellow, 5Y9/9. On the inner surface of the outside petal, there was an area at the base which was near Vivid Yellow, 5Y8/12, while the remainder of the inner surface was between Brilliant Yellow, 2.5Y9/9, and Vivid Yellow, 2.5Y8/12.

The outer surface of the intermediate petal was between Brilliant Yellow, 2.5Y9/9, and Brilliant Yellow, 5Y9/9. The inner surface of the intermediate petal had an area at the base which was near Vivid Yellow, 5Y8/12, the remainder being between Brilliant Yellow, 2.5Y9/9, and Brilliant Yellow, 5Y9/9.

The outer surface of the inside petal was the same coloration as the outer surface of the outside petal, while the inner surface of the inside petal was the same as the inner surface of the intermediate petal.

The description which follows is of a rose that was open for three days in the month of June, having been grown in a greenhouse in Ontario, Calif.:

Both the outer surface and the inner surface of the outside petal had an area at the base which was near Vivid Greenish Yellow, 7.5Y8/12, while the remainder was a pale yellow color which was lighter than Brilliant Yellow, 5Y9/9, but in the same hue.

The inside petal was the same color, on both inner and outer surfaces, as the outside petal.

The general color effect of a newly opened flower was between Brilliant Yellow, 2.5Y9/9, and Vivid Yellow, 2.5Y8/12. After being three days open, the color effect was a pale yellow, lighter than Brilliant Greenish Yellow, 7.5Y9/8.

The petals drop off cleanly, except for petaloids, and are not particularly affected by cold, hot, wet, or dry weather. On the bush in can in the greenhouse, blooms last from 4 to 5 days in the month of June. Roses cut from plants grown in the greenhouse and kept at living-room temperatures last from 3 to 5 days in the month of August.

REPRODUCTIVE ORGANS

Stamens: Average in number, arranged regularly about the pistils, a few being mixed with petaloids.

Filaments: Short to medium-length, being from 3/16" to 1/4" long. They are near Brilliant Greenish Yellow, 7.5Y9/8, almost always without red overcasting, and most with anthers.

Anthers: Small to medium in size, all opening approximately at once. On the upper side they are near Brilliant Yellow, 5Y9/9, with margins near Strong Orange Yellow, 7.5Y7/11. On the under side of the coloration is the same as the upper side.

Pollen: Moderate in amount, and near Strong Orange Yellow, 7.5YR7/11, in color.

Pistils: Average in number, approximately 80.

Styles: From even to uneven, of average length, thin in caliper, and loosely bunched.

Stigma: Near Brilliant Yellow, 2.5Y9/9, in color.

Ovaries: Both enclosed in and protruding from the calyx.

Hips: None available.

FOLIAGE

Leaves are compound, usually 3 to 7 leaflets. They are normal to abundant, medium size, moderately heavy to somewhat leathery, and semi-glossy. Leaflets are nearly round to ovate, with apex mucronate, base obtuse, and margin irregularly serrate.

The color of the mature leaf on the upper surface is between Moderate Olive Green, 5GY4/3, and Grayish Olive Green, 5GY3/2. The under surface of the mature leaf is grayer than a color between Strong Yellow Green, 2.5GY6/8, and Moderate Yellow Green, 2.5GY5/5.

The color of the young foliage on the upper surface is near Strong Yellow Green, 5GY6/8, moderately overlaid with near Moderate Reddish Brown, 7.5R3/6, near the margins. The under surface is between Strong Yellow Green, 5GY7/10, and Strong Yellow Green, 5GY6/8, lightly overlaid along the margins with near Dark Red, 2.5R3/7.

The rachis is light to average size, the upper side being grooved, with some stipitate glands on the edges, the under side being sometimes smooth or with stipitate glands, or sometimes slightly prickly and with stipitate glands.

The stipules are medium-length, moderately narrow, with medium-length narrow points turning out at an angle of less than 90°.

The plant exhibits more than average resistance to mildew, when compared to other varieties now in commerce, and grown under equivalent conditions.

In growth habit, the plant is bushy, upright, and much branched. Its growth is very vigorous, and its canes are of medium caliper.

The main stems are near Moderate Yellowish Green, 7.5GY5/7, much-streaked with between Brownish Orange, 5YR5/8, and Strong Brown, 5YR4/5. There are a very few large prickles, and these are short to medium-length, almost straight, and with moderately short, moderately narrow base. Their color is between gray and Strong Brown, 5YR4/5. There are a very few small prickles, and these are the same color as the large prickles. There are no hairs.

The branches are between Moderate Yellow Green, 5GY5/6, and Moderate Olive Green, 5GY4/3. There are a very few large prickles which are almost straight, with moderately short, moderately narrow base. They are between Strong Yellowish Brown, 10YR5/6, and Moderate Brown, 7.5YR4/5. There are no small prickles and no hairs.

The new shoots are between Strong Yellow Green, 5GY7/10, and Strong Yellow Green, 5GY6/8. There are usually no prickles, large or small, and no hairs.

We claim:

1. A variety of rose plant of the floribunda class substantially as herein shown and described comprising in combination a plurality of the following characteristics, namely, a vigorous habit of growth, a tendency to carry many of its blooms singly, on relatively straight and long stems which are relatively free of thorns and prickles; the strong, spicy fragrance; the brilliant yellow of the freshly-opened bloom, with less than usual fading as the flower matures; the blooms being from 2½ to 3¼ inches in diameter when grown under favorable conditions in Southern California, and comprising from 30 to 50 petals, all undulate, and from 2 to 6 petaloids, with about 80 pistils per bloom; the plant displaying somewhat better than average resistance to mildew under comparable conditions.

No references cited.

ROBERT E. BAGWILL, Primary Examiner